US011096881B2

(12) United States Patent
Kasraee

(10) Patent No.: US 11,096,881 B2
(45) Date of Patent: Aug. 24, 2021

(54) USE OF THIOPHOSPHATE DERIVATIVES AS SKIN DEPIGMENTING AGENTS

(71) Applicant: Scientis, SA, Geneva (CH)

(72) Inventor: Behrooz Kasraee, Geneva (CH)

(73) Assignee: Scientis, SA, Geneva (CH)

(*) Notice: Subject to any disclaimer, the term of this patent is extended or adjusted under 35 U.S.C. 154(b) by 320 days.

(21) Appl. No.: 16/304,953

(22) PCT Filed: May 26, 2017

(86) PCT No.: PCT/EP2017/062746
§ 371 (c)(1),
(2) Date: Nov. 27, 2018

(87) PCT Pub. No.: WO2017/207428
PCT Pub. Date: Dec. 7, 2017

(65) Prior Publication Data
US 2020/0315940 A1 Oct. 8, 2020

(30) Foreign Application Priority Data

May 29, 2016 (CH) ................................ CH00685/16

(51) Int. Cl.
*A61K 8/55* (2006.01)
*A61Q 5/08* (2006.01)
*A61Q 19/02* (2006.01)

(52) U.S. Cl.
CPC .................. *A61K 8/55* (2013.01); *A61Q 5/08* (2013.01); *A61Q 19/02* (2013.01)

(58) Field of Classification Search
None
See application file for complete search history.

(56) References Cited

U.S. PATENT DOCUMENTS

2009/0005349 A1    1/2009    Gaillard et al.

FOREIGN PATENT DOCUMENTS

| CA | 1157774 A | 11/1983 |
| CH | 706226 A2 | 9/2013 |
| EP | 0897717 A2 | 2/1999 |
| FR | 2988601 A1 | 10/2013 |
| JP | 2002293711 A | 10/2002 |
| WO | 00/40209 A2 | 7/2000 |

OTHER PUBLICATIONS

Chavin W; Schlesing W., Naturwissenschaften, 1966; vol. 53; No. 16; pp. 413-414, XP002772973.
Bleehen S.S., Journal of the Society Cosmetic Chemists, Society of Cosmetic Chemists, 1977; vol. 28; pp. 407-412, XP000910474.
Akerfeldt, S., Acta Radiologica: Therapy, Physics, Biology, 1963, vol. 1; No. 6; pp. 465-470.
Akerfeldt, S., Acta Chem. Scand., 1962; vol. 16; No. 7; pp. 1813-1815.
Bedwell, J. et. al., Photochemistry and Photobiology, 1991; vol. 53; No. 6; pp. 753-756.
Schneider, J.A. and Dahil, R., Pediatr Nephrol, 2008; vol. 23; pp. 1907-1923.

*Primary Examiner* — Jennifer A Berrios
(74) *Attorney, Agent, or Firm* — Dinsmore & Shohl LLP; Weston R. Gould

(57) ABSTRACT

The present invention relates to a skin depigmentation composition comprising (i) at least one thiophosphate derivative and (ii) acceptable carriers for topical, oral and/or parenteral administrations to human. The present invention further relates to the cosmetic and medical treatment uses thereof for reducing skin and/or hair pigmentation.

8 Claims, No Drawings

USE OF THIOPHOSPHATE DERIVATIVES AS SKIN DEPIGMENTING AGENTS

FIELD OF THE INVENTION

The present invention relates to a skin depigmentation composition comprising (i) at least one thiophosphate derivative and (ii) acceptable carriers for topical, oral and/or parenteral administrations to human. The present invention further relates to the cosmetic and medical treatment uses thereof for reducing skin and/or hair pigmentation.

BACKGROUND OF THE INVENTION

Human skin and hair colours are quite variable around the world. Cutaneous coloration in humans arises from a complex series of cellular processes that are carried out within the melanocytes located in the lower part of the epidermis and within the hair follicles. These processes result in the synthesis and transfer of a pigment, melanin, which, besides being responsible for skin color and tone, is the key physiological defense against sun-induced damage, such as sunburn, photoaging and photocarcinogenesis.

Hyperpigmentation, hypopigmentation, and other pigmentation disorders are quite common and can arise from a number of causes including excessive sun exposure, medications and the like. Common pigmentation disorders include melasma (dark patches experienced during or after pregnancy) and liver spots (which often develop with age), and may arise as a side effect of birth control pills, and/or as a persistent result of acne, burns, bites and other skin injuries. Similarly, freckles, melasma and pigmentary deposits after sun exposure tend to occur or increase or become difficult to disappear with increasing age, thus being one of the more disconcerting and/or common problems of skin care for persons of middle to advanced age.

Post inflammatory hyper-pigmentation might occur following any inflammatory state of the skin such as chemical burns or following laser therapy.

In an effort to simply obtain brighter/lighter skin or address the pigmentation disorders, various compositions have been formulated. The use of such compositions is not limited for use in treating pigmentation disorders but is also used in some cultures/markets merely for the purpose of changing or modifying ones natural healthy skin and/or hair colour.

A large number of agents and methods for skin depigmentation have been developed and put on the market. Such methods include the oral administration of large doses of Vitamin C, the parenteral administration of glutathione, the topical administration of peroxide bleaching agents such as hydrogen peroxide for skin and hair depigmentation, zinc peroxide, sodium peroxide and the like, and the topical application of Vitamin C and/or cysteine. Vitamin C, however, has stability issues, especially in water based formulations, resulting in colour and odour changes.

The most commonly employed depigmentation agent has been hydroquinone and its derivatives. However, these compounds, while effective, have serious, detrimental side effects. Even at concentrations below 2%, hydroquinone is both irritating and cytotoxic to the melanocytes. Similar problems have been experienced with hydrogen peroxide depigmentation agents as well. Another known depigmentation agent is tretinoin, an effective treatment for both wrinkles and skin pigmentation but is also known to cause skin irritation that can lead to skin darkening.

A wide-range of polyphenols present in plant extracts have also been used for skin depigmentation purposes. Such natural polyphenols are for example anthraquinones, arylbenzofurans, chalcones, coumarins, and flavonoids. One class of polyphenols compounds that has received a lot of attention is that based on substituted resorcinols and their derivatives. However, despite their relatively good skin lightening capabilities, they tend to suffer from stability issues, which also oftentimes coincide with loss of skin lightening efficacy, rendering them generally unsuitable for topical applications.

Another agent, which demonstrated interesting depigmentation effects is nicotinamide. Nicotinamide is a 3-substituted pyridine which exerts its skin depigmenting effect through the inhibition of melanosomal transfer from melanocytes to keratinocytes. Despite good tolerability on human skin, nicotinamide has a poor skin depigmenting efficacy and does not exhibit any hair lightening effect.

Consequently there is still a need for a skin/hair depigmentation composition that provides effective lightening capabilities and does not cause significant inflammation, irritation, or photosensitivity of the skin following application.

Many thiols (molecules containing the SH-moiety) exert considerable skin depigmenting activity. Examples are parathiophenol, thio-ethylamine hydrochloride and di-methylmercaptoethylamine hydrochloride. However, despite considerable skin depigmenting activity, thiols are usually non-utilizable in skin depigmenting products because of two major characteristics: i) thiols are usually irritant to the skin when used topically ii) these molecules are usually very mal-odorous and produce an offensive "skunky" odor in the products; this significantly limits their use in cosmetic products intended for skin depigmentation, and iii) thiols are usually unstable molecules and are readily oxidized in contact with air or oxidizing agents. Thiols lose their depigmenting activity after being oxidized. The problem of stability is thus one of the major problems of products containing thiols.

The ideal skin depigmentation composition should have a potent, rapid and selective depigmentation effect on melanocytes, carry no short- or long-term side-effects and lead to a permanent removal of undesired pigment, acting at one or more steps of the pigmentation process. To be acceptable as a cosmetic product, the composition should not have any bad odor and must be stable enough in order to have an acceptable shelf-life.

SUMMARY OF THE INVENTION

An aspect of the present invention provides a skin and/or hair depigmentation composition comprising
(i) a depigmentation effective amount of a thiophosphate derivative of formula I:

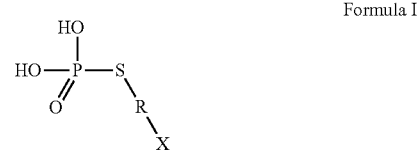

Formula I or pharmaceutically acceptable salts thereof, wherein:
R is a $C_1$-$C_{18}$ saturated or unsaturated, linear, branched, cyclic or aromatic hydrocarbon group, X is selected from the group comprising H, —OH, —SH, $C_1$-$C_{18}$ saturated or unsaturated, linear, branched, cyclic or aromatic hydrocarbon group, and —$NR_1R_2$ represented by the Formula A:

Formula A wherein
$R_1$ is selected from the group comprising H, —OH, —SH, $C_1$-$C_{18}$ saturated or unsaturated, linear, branched, cyclic or aromatic hydrocarbon group,
$R_2$ is selected from the group comprising H, —OH, —SH, $C_1$-$C_{18}$ saturated or unsaturated, linear, branched, cyclic or aromatic hydrocarbon group,
provided that when R is —$CH_2$—$CH_2$—, $R_1$ is not H, or
provided that cysteamine-S-phosphate is excluded, and
(ii) acceptable carriers for topical, oral and/or parenteral administrations.

Another aspect of the present invention provides use of the skin and/or hair depigmentation composition of the invention for preventing and/or reducing pigmentation of normal skin and/or normal hair.

Another aspect of the present invention provides a skin depigmentation composition of the invention for use in a method for preventing and/or reducing skin pigmentation disorders related to an abnormal excessive production of melanin or abnormal increased number of melanocytes.

Another aspect of the present invention provides a method for preventing and/or reducing pigmentation of normal skin and/or hair, comprising topically applying the skin and/or hair depigmentation composition of the invention to the skin and/or hair of the subject in need thereof.

Another aspect of the present invention provides a method for preventing and/or reducing skin pigmentation disorders, comprising topically applying the skin depigmentation composition of the invention to the skin of the subject in need thereof.

Another aspect of the present invention provides a method for preventing and/or reducing skin pigmentation disorders, comprising oral or parenteral administration of the skin depigmentation composition of the invention to the subject in need thereof.

DETAILED DESCRIPTION OF THE INVENTION

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. Also as used in the specification and claims, the language "comprising" can include analogous embodiments described in terms of "consisting of" and/or "consisting essentially of".

As used in the specification and claims, the singular form "a", "an" and "the" include plural references unless the context clearly dictates otherwise.

As used in the specification and claims, the term "and/or" used in a phrase such as "A and/or B" herein is intended to include "A and B", "A or B", "A", and "B".

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein the terms "subject" are well-recognized in the art, and, are used herein to refer to a mammal, and most preferably a human. In some embodiments, the subject is a subject in need of treatment or a subject with a skin pigmentation disease or disorder, such as hyperpigmentation. However, in other embodiments, the subject can be a normal subject who has a normal healthy skin and who needs to lighten (whiten) his skin. The term does not denote a particular age or sex. Thus, adult and newborn subjects, whether male or female, are intended to be covered.

As used herein the term "depigmentation" (or lightening, bleaching, whitening and brightening used interchangeably herein) is the lightening of the skin and/or hair, or loss of pigment. The skin depigmentation agents or compositions are also referred as "skin lightener", "skin whitener", "skin even-toner" and "skin brightener". The hair depigmentation agents or compositions are referred to as "hair lightener", "hair whitener" and "hair brightener". Whatever terminology is employed, the general premise is that they all relate to a reduction in the melanization or rate of melanization of the skin and/or hair, which results in loss of pigment.

As used herein the term "acceptable carriers" means that the compositions or components thereof so described are suitable for use in contact with skin and/or hair of human, or suitable for any other means of administration to human body without undue toxicity, incompatibility, instability, irritability, allergic response, and the like.

As used herein the term "topical" or "topically" refers to the application of the composition of the present invention onto the surface of the skin and/or a portion thereof such as hair.

As used herein the term "administration" to human body refers to any means of introducing the composition of the present invention onto and/or into the human body or a portion thereof (eg. oral use, use of skin patches, injections, suppository use, inhalation, etc).

As used herein the term "depigmentation effective amount" means an amount of a compound or composition sufficient to significantly induce a positive benefit, preferably a reduction in the melanization or rate of melanization of the skin and/or hair, but low enough to avoid serious side effects.

As used herein the term "post-inflammatory hyperpigmentation" refers to the changes in melanin content as a response to an inflammatory event (e.g., acne, scratch, laser therapy, insect sting or bite, sunburn, etc), especially in individuals of darker skin tone or colour.

Melanin synthesis or melanogenesis in mammalian skin occurs in epidermal melanocytes. The so formed melanin is accumulated/deposited in melanosomes, vesicles found within the melanocyte cells, which are subsequently transferred from the melanocytes and taken up and internalized by the keratinocytes, which then carry them to the surface of the skin. Usually skin coloration is primarily regulated by the amount and type of melanin synthesized by the epidermal melanocyte. This synthesis process starts through the hydroxylation of the amino acid tyrosine to DOPA which is further oxidized to dopaquinone. Both these steps are accomplished by the enzyme tyrosinase. Dopaquinone is then spontaneously converted to dopachrome which further gives rise to the two indolic melanin monomers dihydroxyindole and dihydroxyindole-2-carboxylic acid. These monomers are in turn metabolized by the peroxidase —$H_2O_2$ system to produce eumelanin (brown-black melanin). Pheomelanin (yellow-red melanin) would be formed if dopaquinone encounters cellular thiols such as glutathione or cysteine. The peroxidase —$H_2O_2$ system plays an important role in the metabolisation of pheomelanin intermediates to form pheomelanin pigments (Dermatology. 2002; 205: 329-39.

Typically depigmentation can be achieved by regulating (i) the transcription and activity of tyrosinase, tyrosinase related protein-1 (TRP-1), tyrosinase related protein-2 (TRP-2), and/or peroxidase; (ii) the uptake and distribution of melanosomes in recipient keratinocytes and (iii) melanin and melanosome degradation and turnover of "pigmented" keratinocytes.

The involvement of peroxidase in the polymerization of melanogenic intermediates has been suggested by the high efficiency of peroxidase in the oxidation of 5,6-dihydroxyindole (DHI) with the generation of hydrogen peroxide ($H_2O_2$) as a by-product. Intracellular $H_2O_2$, generated after UV irradiation or in response to cytokines, such as tumour necrosis factor-α (TNF-α) or transforming growth factor-β (TGF-β), can induce a transient reduction of tyrosinase and other melanogenic protein activities, through the down-regulation of the MITF transcription factor. However, it provides the peroxidase-$H_2O_2$ system with hydrogen peroxide and thus induces the peroxidase dependent steps in melanogenesis process such as the polymerization of indolic eumelanin monomers DHI and DHICA. The inhibition of peroxidase, reducing the polymerization rate of eumelanin monomers, results in depigmentation.

The Applicant has surprisingly found that the topical application of thiophosphate derivatives, such as 2-di-isopropylaminoethanthiophosphate, 2-di-phenylaminoethanthiophosphate or para-phenol-thiophosphate produces skin and/or hair depigmentation when applied to human skin.

An aspect of the present invention provides a skin and/or hair depigmentation composition comprising
(i) a depigmentation effective amount of a thiophosphate derivative of formula I:

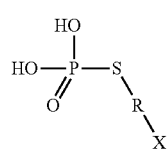

Formula I or pharmaceutically acceptable salts thereof, wherein:

R is a $C_1$-$C_{18}$ saturated or unsaturated, linear, branched, cyclic or aromatic hydrocarbon group, X is selected from the group comprising H, OH, SH, $C_1$-$C_{18}$ saturated or unsaturated, linear, branched, cyclic, aromatic hydrocarbon group, and —$NR_1R_2$ represented by the Formula A:

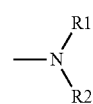

Formula A wherein
$R_1$ is selected from the group comprising H, —OH, —SH, $C_1$-$C_{18}$ saturated or unsaturated, linear, branched, cyclic or aromatic hydrocarbon group,
$R_2$ is selected from the group comprising H, —OH, —SH, $C_1$-$C_{18}$ saturated or unsaturated, linear, branched, cyclic or aromatic hydrocarbon group,
provided that when R is —$CH_2$—$CH_2$—, $R_1$ is not H or provided that cysteamine-S-phosphate is excluded, and
(ii) acceptable carriers for topical, oral and/or parenteral administrations.

In some preferred embodiments of the invention, in thiophosphate derivative of formula I,
R is benzene ring or —$CH_2$—$CH_2$—,
X is selected from the group comprising OH, di-isopropylamine, di-phenylamine, di-etylamine, di-methylamine.

In other preferred embodiments of the invention, in thiophosphate derivative of formula I,
R is —$CH_2$—$CH_2$—,
X is selected from the group comprising OH, di-isopropylamine, di-phenylamine, di-etylamine, di-methylamine.

In further preferred embodiments of the invention, in thiophosphate derivative of formula I,
R is benzene ring or —$CH_2$—$CH_2$—; preferably R is —$CH_2$—$CH_2$—.

In other preferred embodiments of the invention, in thiophosphate derivative of formula I,
X is selected from the group comprising OH, di-isopropylamine, di-phenylamine, di-etylamine, di-methylamine.

The term "$C_1$-$C_{18}$ saturated or unsaturated, linear or branched hydrocarbon groups" as used herein refers to saturated or unsaturated, linear (straight) or branched chain hydrocarbon radicals derived from a hydrocarbon moiety containing between one and eighteen carbon atoms, such as, bit not limited to, methyl, ethyl, propyl, isopropyl, n-butyl, tert-butyl, neopentyl, n-hexyl, n-heptyl, n-octyl, n-nonyl, n-decyl, n-undecyl and n-docecyl. In some preferred embodiments, in the thiophosphate derivative of formula I, $C_1$-$C_{18}$ saturated or unsaturated, linear or branched hydrocarbon group is selected from the group comprising methyl, ethyl, propyl, isopropyl, n-butyl, tert-butyl, neopentyl, n-hexyl, n-heptyl, n-octyl, n-nonyl, n-decyl, n-undecyl and n-docecyl.

"$C_1$-$C_{18}$ cyclic or aromatic hydrocarbon group" refers to a saturated or partially saturated, monocyclic or fused or spiro polycyclic, such as cyclopropyl, cyclobutyl, cyclopentyl, cyclohexyl and the like. It includes monocyclic systems such as cyclopropyl and cyclohexyl, bicyclic systems such as decalin, and polycyclic systems such as adamantane. The group may be a terminal group or a bridging group. The aromatic hydrocarbon group is also included and refers to a benzene ring or derivatives thereof. In some preferred embodiments, in thiophosphate derivative of formula I, $C_1$-$C_{18}$ cyclic or aromatic hydrocarbon group is selected from the group comprising cyclopropyl, cyclobutyl, cyclopentyl, cyclohexyl and benzene.

In other preferred embodiments, thiophosphate derivative of the present invention is selected from the group comprising 2-di-isopropylaminoethanethiophosphate, 2-diphenylaminoethanethiophosphate, 2-dimethylaminoethanethiophosphate, and para-phenol-thiophosphate or pharmaceutically acceptable salts thereof.

In further preferred embodiments, thiophosphate derivative of the present invention is selected from the group comprising 2-di-isopropylaminoethanethiophosphate, 2-diphenylaminoethanethiophosphate and para-phenol-thiophosphate.

In further preferred embodiments, thiophosphate derivative of the present invention is selected from the group comprising 2-di-isopropylaminoethanethiophosphate, and 2-diphenylaminoeth anethiopho sphate.

In addition to thiophosphate derivatives of the Formula (I), the thiophosphate derivatives of the present invention include pharmaceutically acceptable salts thereof.

The term "pharmaceutically acceptable salts" as used herein refers to salts that retain the desired biological activity of the thiophosphate derivatives of the present invention, and include pharmaceutically acceptable acid addition salts and base addition salts. Suitable pharmaceutically acceptable acid addition salts of the thiophosphate derivatives of Formula (I) may be prepared from an inorganic acid or from an organic acid, or can be prepared in situ during the final isolation and purification of the thiophosphate derivatives of the invention. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of the thiophosphate derivatives of Formula (I) include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formula.

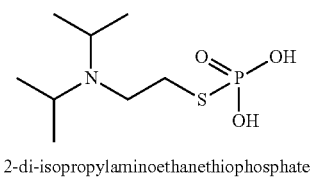

2-di-isopropylaminoethanethiophosphate

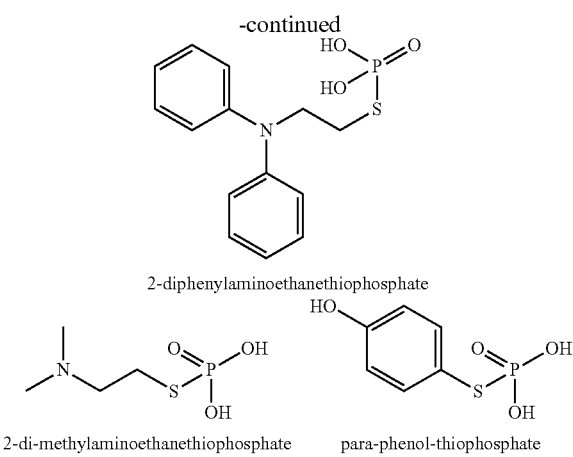

2-diphenylaminoethanethiophosphate 2-di-methylaminoethanethiophosphate    para-phenol-thiophosphate According to an embodiment of the present invention, the Applicant has shown, for the first time, that the repeated topical application of a thiophosphate of the present invention, preferably 2-di-isopropylaminoethanethiophosphate or 2-diphenylaminoethanethiophosphate, onto the human skin produces skin depigmentation without any signs of skin irritation or inflammation and that 2-di-isopropylaminoethanethiophosphate or 2-diphenylaminoethanethiophosphate are each significantly more effective and less irritating to the skin compared with their non-phosphated counterparts the 2-di-isopropylaminoethanethiol and 2-diphenylaminoethanethiol. In addition, the Applicant introduces for the first time thiophosphates as odorless skin depigmenting agents compared to their non-phosphated thiol counterparts, which have offensive skunky odors that prohibit their use in cosmetic products. For example the 2-di-isopropylaminoethanethiophosphate and 2-diphenylaminoethanethiophosphate are odorless skin depigmenting agents while their non-phosphated depigmenting counterparts the 2-di-isopropylaminoethanethiol and 2-diphenylaminoethanethiol have offensive skunky odors. The Applicant also hound that the phosphated depigmenting thiols were significantly more stable when exposed to heat and moisture, compared to their non phosphated thiol counterparts.

The skin depigmentation composition of the present invention may contain a concentration of one or more thiophosphate, preferably selected from the group comprising of about 0.001-50%, preferably 0.01-10.0%, most preferably 0.1-5.0% by weight of the composition.

The skin depigmentation compositions of the invention may be cosmetic, dermatologic, or pharmaceutical compositions, and may exist in a wide variety of forms for topical, oral or parenteral administration to human. These compositions can be intended for topical application, such as emulsions, suspensions, solutions and the like. In certain embodiments, the compositions of the invention are in the form of lotions, creams, gels, solutions, sprays, cleansers, powders, ointments, waxes, lipsticks, patches, soaps, shampoos, hydroalcoholic solutions, suspensions, scrubs, saturated pads, skin or hair conditioning agents, and other types of cosmetic compositions. In further embodiments, the compositions of the invention may be, for example anhydrous preparations, oil-free preparations, emulsions or microemulsions of the type water-in-oil (W/O) or of the type oil-in-water (O/W), multiple emulsions, for example of the type water-in-oil-in-water (W/O/W), solid sticks, or even aerosols.

The preferred form of the topical skin depigmentation composition of the present invention is an oil in water hydrophil cream (vanishing cream) containing stearic acid, petrolatum, cetyl alcohol, paraffin, sorbitol, glycerin, triethanolamine, pottasium sorbate, sodium benzoate, butylated hydroxytoluene and distilled water together with 5% (w/w) 2-di-isopropylaminoethanethiophosphate.

The skin depigmentation compositions of the invention may be administered to human in an oral form. The compositions can be intended for oral intake by human, such as tablets, capsules, powders, aquaous or non.aquous solutions, syrups and the like.

The skin depigmentation compositions of the invention may be administered parenterally to human. The composition can be intended for parenteral use in human, such as injections (all forms of injection such as intravenous, intra-arterial, intra-muscular, intra-dermal or sub-cutaneous injections etc), inhalation, sub-lingual, suppository and the like.

For administration, the cosmetic or dermatologic compositions of the invention may be applied to the skin and/or hair (to body surface) in adequate depigmentation effective amount in the manner conventional for cosmetics and which has a topical effect, i.e. local effect contrasting with systemic effects. The oral or parenteral compositions of the invention can be administered to human in adequate depigmentation effective amount in the manner conventional for oral and parenteral products and which has a skin and/or hair depigmenting effect after repeated administrations.

The skin depigmentation compositions of the invention contain acceptable carriers for topical, oral or parenteral use, as are used conventionally in such compositions, for example preservatives, antioxidants, bactericides, fungicides, solvents, perfumes, substances for preventing foaming, dyestuffs, pigments which have a colouring effect, thickeners, propellants, surfactant substances, emulsifiers, softening, moisturizing and/or moisture-retaining substances, distilled water, fats, oils, waxes or other conventional constituents of a topical, oral or parenteral composition, such as alcohols, polyols, polymers, foam stabilizers, electrolytes, organic solvents or silicone derivatives. The necessary amounts of the acceptable carriers can, based on the desired product, easily be chosen by a person skilled in the art.

A moisturizing substance may be incorporated into those skin depigmentation compositions of the present invention which are intended for topical use, to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil, aloe extracts, fatty acids such as oleic and stearic, fatty alcohols such as cetyl and hexadecyl (ENJAY), diisopropyl adipate, hydroxybenzoate esters, benzoic acid esters of $C_9$-$C_{15}$-alcohols, isononyl iso-nonanoate, ethers such as polyoxypropylene butyl ethers and polyoxypropylene cetyl ethers, and $C_{12}$-$C_{15}$-alkyl benzoates, and mixtures thereof. Moisturizing substances that bind water, thereby retaining it on the skin surface are called humectants. Suitable humectants can be incorporated into the skin depigmentation compositions of the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof.

The skin depigmentation compositions of the present invention can also contain the usual alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or monoethylether and analogue products, polymers, foam stabilizers; electrolytes and especially one or more thickeners.

Thickeners that may be used in the skin depigmentation compositions of the present invention to assist in making the consistency of a product suitable include carbomer, siliciumdioxide, magnesium and/or aluminium silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof.

Suitable neutralizing agents which may be included in the skin depigmentation compositions of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing.

The skin depigmentation composition of the present invention may also contain filter substances that absorb UV radiation, or sunscreens, wherein the total quantity of filter substances is, for example 0.001 to 30%, preferably 0.5 to 10%, based on the total weight of the preparation. The compositions may also serve as sunscreen agents for the skin. Such UV filter substances include, for example, the following: avenobenzene, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, and zinc oxide.

The skin and/or hair depigmentation compositions of the present invention may also include one or more skin penetrants. These are additives that, when applied to the skin, have a direct effect on the permeability of the skin barrier: increasing the speed with which and/or the amount by which certain other compounds are able to penetrate into the skin layers. Exemplary organic penetration enhancers include dimethyl sulfoxide; isopropyl myristate; decyl, undecyl or dodecyl alcohol; propylene glycol; polyethylene glycol; $C_9$-$C_{11}$ or $C_{12}$-$C_{15}$ fatty alcohols; azone; alkyl pyrrolidones; diethoxy glycol (Transcutol); lecithin; etc. Surfactants can also be used as penetration enhancers.

The skin and/or hair depigmentation composition of the present invention may also include a skin and/or hair benefit agent selected from the group comprising alpha-hydroxy acids, beta-hydroxy acids, polyhydroxy acids, nicotinamide, isonicotinamide, picolinamide, kojic acid, arbutin, deoxyarbutin, depigmenting oligopeptides, soybean extract, licorice extract, phyllanthus emblica extract, Bellis perennis extract, glabridin, polyphenol antioxidants, thiolic antioxidants, cysteamine hydrochloride, hydroquinone, methimazole, t-butyl hydroquinone, Vitamin C derivatives, Vitamin E derivatives (such as tocopherols), pyridines, Vitamin B derivatives (such as thiamines), dioic acids, retinoids, corticosteroids, 4-substituted resorcinol derivatives, tranexamic acid, ebselen, and mixtures thereof.

In some preferred embodiments, Vitamin C derivatives consist of the ascorbic acid fragment (ascorbyl) and a fragment of another acid (such as palmitate or phosphate). The preferable Vitamine C derivatives are ascorbyl palmitate and magnesuim ascorbyl phosphate.

The skin and/or hair depigmentation compositions of the present invention may also include liposomes (unilamellar and/or multilamellar liposomes of any size) in order to facilitate the delivery of any component(s) of the depigmenting composition to its site of action. The optimal type and size of liposome(s) and the nature of the medium in which the liposomes are dispersed, can be easily chosen by a person skilled in the art.

The present invention further provides the use of the skin and/or hair depigmentation composition of the invention for preventing and/or reducing pigmentation of normal skin and/or normal hair. The depigmentation composition of the present invention may cause the hair to turn lighter compared to its natural colour. For example, it may cause the hair to turn brown, red or blonde compared to its natural black colour. Said skin and hair is preferably at least one of facial skin and/or facial hair, skin and/or hair on the neck, skin and/or hair on the arms, skin and/or hair on the hands, skin and/or hair on the legs and skin and/or hair on the scalp. The terms "normal skin" and "normal hair" are referred to healthy skin and healthy hair having no pigmentation disorders.

The present invention also provides a skin depigmentation composition of the invention for use in a method for preventing and/or reducing skin pigmentation disorders.

In preferred embodiments of the invention, the skin pigmentation disorders, such as non-cosmetic disorders, lesions and/or damages, are related to an abnormal excessive production of melanin or abnormal increased number of melanocytes.

Increased production and accumulation of melanins characterize a large number of skin (epidermal and/or dermal) pigmentation disorders, which include acquired hyperpigmentation, such as melasma, postinflammatory hyperpigmentation, solar lentigo, senile lentigo, etc. Epidermal and dermal hyperpigmentation can be dependent on either increased numbers of melanocytes or activity of melanogenic enzymes. Ultraviolet light, hormones, chronic inflammation, and rubbing of the skin as well as abnormal α-melanocyte stimulating hormone (α-MSH) release, are triggering factors for these disorders.

In preferred embodiments of the invention, pigmentation disorders are selected from the group comprising hyperpigmentation, melasma, postinflammatory hyperpigmentation, lentigo, freckles (preferably freckles due to an abnormal excessive production of melanin), drug induced hyperpigmentation, light induced hyperpigmentation and chemical induced hyperpigmentation.

The present invention also provides a method for preventing and/or reducing pigmentation of normal skin and/or normal hair, comprising the topical, oral, or parenteral administration of the skin and/or hair depigmentation composition of the invention to the subject in need thereof.

The present invention also provides a method for reducing pigmentation of normal skin, in patients with generalized vitiligo in order to reduce the contrast between the diseased and the normal skin.

The present invention further provides a method for preventing and/or reducing skin pigmentation disorders, comprising topical, oral and/or parenteral administration of the skin depigmentation composition of the invention to the subject in need thereof.

The term "preventing" as used herein, means that the normal (healthy) pigmentation or disease related pigmentation would not occur on the skin, preferably human skin. The term "reducing" as used herein, means that a significant reduction in the formation or rate of formation of pigmentation of the skin and/or hair, preferably human skin and/or hair, is induced.

In the method according to the invention the skin and/or hair depigmentation compositions are applied to the skin and/or hair, preferably human skin and/or hair or skin and/or hair of the subject in need thereof. The amount of the skin and/or hair depigmentation composition that is to be applied to the skin and/or hair depends upon the form of the skin/hair depigmentation composition and its mode of application. For example, a spray formulation may be applied so as to provide a light, even coat on the skin and/or hair. Similarly, lotions, creams, gels, shampoos and the like are typically applied in an amount to provide a light coating to the treatment area: consistent with the application of topical pharmaceutical ointments, creams, lotions, and the like. Generally the rate of application, especially where all or substantially all of the skin surface, including hairy or non-hairy skin, is to be treated, is about 20 to 60 ml for the entire body, i.e., for the exposed skin of an "average individual" wearing a swimsuit and standing 1.65 m tall, weighing 68 kg, and having a 0.81 m waist. This translates to an application rate of about 2 mg/cm$^2$ of skin surface, including hairy or non-hairy skin surface. On the face, a typical application rate is 1.2 to 1.7 ml. At such levels of application, the amount of skin and/or hair depigmentation solution applied lies in the range of from about 0.1 to about 10 mg/cm$^2$, preferably from about 1 to about 3 mg/cm$^2$, of skin and/or hair.

The compositions of the invention may be administered topically, orally or parenterally, once or more times per day depending on different factors including the activities the particular subject is engaged in. For example, a subject engaging in normal workday activities may wish to apply the compositions twice a day, once in the morning, and once in the evening, in conjunction with normal grooming. On the other hand, if the subject plans outdoor activities such as sunbathing and athletics, the compositions may be administered prior to, and during, such activities, much like a sunscreen composition is applied periodically during the day. The compositions may be used for hyperpigmentation on the face and neck, or to alter the dark normal colour of the scalp or body hair to a lighter colour by applying the appropriate skin and/or hair depigmentation compositions to the scalp, face and neck areas. However, the skin and/or hair depigmentation compositions of the present invention may also be applied to the entire body, particularly areas which are not covered by clothing, such as the arms, neck, and lower legs.

The skin depigmentation compositions of the present invention can be prepared by any method known in the art for cosmetic, dermatological or pharmaceutical compositions. Generally, the method comprises the simple mixing or blending of the components; though, especially where insoluble or immiscible components are employed higher agitation or homogenization may be necessary to prepare an appropriate composition, e.g., an emulsion or suspension, etc. Additionally, during the preparation, it may be desirable to add known pH adjusters, in order to maintain a proper pH of the composition for topical application, or oral or parenteral administrations, especially if basic ingredients are to be employed. Generally, the pH should be on the neutral to slightly acidic or slightly basic side, perhaps as low as pH 4 and as high as pH 8. Preferably, though, the pH will be in the range of from about 5 to about 6.9.

Further instances of the present disclosure:

1. A skin and/or hair depigmentation composition comprising
   (ii) a depigmentation effective amount of a thiophosphate derivative of formula I:

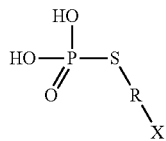

Formula I or pharmaceutically acceptable salts thereof
wherein:
   R is a $C_1$-$C_{18}$ saturated or unsaturated, linear, branched, cyclic or aromatic hydrocarbon group,
   X is selected from the group comprising H, —OH, —SH, $C_1$-$C_{18}$ saturated or unsaturated, linear, branched, cyclic or aromatic hydrocarbon group, and —$NR_1R_2$ represented by the Formula A:

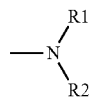

Formula A wherein
   $R_1$ is selected from the group comprising H, —OH, —SH, $C_1$-$C_{18}$ saturated or unsaturated, linear, branched, cyclic or aromatic hydrocarbon group,
   $R_2$ is selected from the group comprising H, —OH, —SH, $C_1$-$C_{18}$ saturated or unsaturated, linear, branched, cyclic or aromatic hydrocarbon group,
   provided that when R is —$CH_2$—$CH_2$—, $R_1$ is not H, and
(ii) acceptable carriers for topical, oral and/or parenteral administrations.

2. The skin and/or hair depigmentation composition of instance 1, wherein in the thiophosphate derivative of formula I, $C_1$-$C_{18}$ saturated or unsaturated, linear or branched hydrocarbon group is selected from the group comprising methyl, ethyl, propyl, isopropyl, n-butyl, tert-butyl, neopentyl, n-hexyl, n-heptyl, n-octyl, n-nonyl, n-decyl, n-undecyl and n-docecyl.

3. The skin and/or hair depigmentation composition of any one of instances 1-2, wherein in thiophosphate derivative of formula I, $C_1$-$C_{18}$ cyclic or aromatic hydrocarbon group is selected from the group comprising cyclopropyl, cyclobutyl, cyclopentyl, cyclohexyl and benzene.

4. The skin and/or hair depigmentation composition of any one of instances 1-3, wherein R is benzene ring or —$CH_2$—$CH_2$—.

5. The skin and/or hair depigmentation composition of any one of instances 1-4, wherein R is —$CH_2$—$CH_2$—.

6. The skin and/or hair depigmentation composition of any one of instances 1-5, wherein X is selected from the group comprising OH, di-isopropylamine, di-phenylamine, di-etylamine, di-methylamine.

7. The skin and/or hair depigmentation composition of instance 1, wherein said thiophosphate derivative is selected from the group comprising 2-di-isopropylamino-ethanethiophosphate, 2-diphenylaminoethanethiophosphate, 2-dimethylaminoethanethiophosphate, and para-phenol-thiophosphate or pharmaceutically acceptable salts thereof.

8. The skin and/or hair depigmentation composition of instance 1, wherein said thiophosphate derivative is selected from the group comprising 2-di-isopropylamino-ethanethiophosphate, 2-diphenylaminoethanethiophosphate and para-phenol-thiophosphate.

9. The skin and/or hair depigmentation composition of instance 1, wherein said thiophosphate derivative is selected from the group comprising 2-di-isopropylamino-ethanethiophosphate, and 2-diphenylaminoethanethiophosphate.

10. The skin and/or hair depigmentation composition of any one of instances 1 to 9, wherein said skin and hair are a mammal skin and hair, preferably human skin and hair.

11. The skin and/or hair depigmentation composition of any one of instances 1 to 10, wherein said depigmentation composition is in a suitable form for topical application, selected from the group comprising a lotion, a cream, a gel, a solution, a spray, a patch, a cleanser, a powder, an ointment, a wax, a lipstick, a soap, a shampoo, a bath gel, a bath oil, a bath bubble, a hydroalcoholic solution, a suspension, a scrub, a saturated pad, a skin or hair conditioning agent; or in a suitable form for oral administration to human comprising a tablet, a capsule, a powder, a syrup, a gel, a suspension, an aquous or non-aquous solution; or in a suitable form for parenteral administration comprising an injectable solution (for intra-dermal, sub-cutaneous, intra-muscular or intra-venous injections), inhalation spray, suppository or transdermal patch.

12. The skin and/or hair depigmentation composition of any one of instances 1 to 11, wherein said composition further comprises a skin and/or hair benefit agent selected from the group comprising alpha-hydroxy acids, beta-hydroxy acids, polyhydroxy acids, nicotinamide, kojic acid, arbutin, deoxyarbutin, depigmenting oligopeptides, soybean extract, licorice extract, phyllanthus emblica extract, Bellis perennis extract, glabridin, polyphenol antioxidants, thiolic antioxidants, cysteamine hydrochloride, hydroquinone, methimazole, pyridines, t-butyl hydroquinone, Vitamin C derivatives, Vitamin E derivatives, Vitamin B derivatives, dioic acids, retinoids, 4-substituted resorcinol derivatives, tranexamic acid or its derivatives, corticosteroids and mixtures thereof.

13. Use of the skin and/or hair depigmentation composition of any one of instances 1 to 12 for preventing and/or reducing pigmentation of normal skin and/or normal hair.

14. A skin depigmentation composition of any one of instances 1 to 12 for use in a method for preventing and/or reducing skin pigmentation disorders related to an abnormal excessive production of melanin or abnormal increased number of melanocytes.

15. The skin depigmentation composition for use in a method for preventing and/or reducing skin pigmentation disorders of instance 14, wherein said pigmentation disorders are selected from the group comprising hyperpigmentation, melasma, postinflammatory hyperpigmentation, solar or senile lentigo, freckles due to an abnormal excessive production of melanin, drug induced hyperpigmentation, light induced hyperpigmentation and chemical induced hyperpigmentation.

16. A method for preventing and/or reducing pigmentation of normal skin and/or hair, comprising topically applying the skin and/or hair depigmentation composition of any one of instances 1 to 12 to the skin and/or hair of the subject in need thereof.

17. A method for preventing and/or reducing skin pigmentation disorders, comprising topically applying the skin depigmentation composition of any one of instances 1 to 12 to the skin of the subject in need thereof.

18. A method for preventing and/or reducing skin pigmentation disorders, comprising oral and/or parenteral administration of the skin depigmentation composition of any one of instances 1 to 12 to the subject in need thereof.

19. The method of instances 17 or 18, wherein said pigmentation disorders are selected from the group comprising hyperpigmentation, melasma, postinflammatory hyperpigmentation, solar or senile lentigo, freckles, drug induced hyperpigmentation, light induced hyperpigmentation and chemical induced hyperpigmentation.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples, are, however, exemplary of methods of practising the present invention and are not intended to limit the scope of the invention.

EXAMPLES

Example 1

Six different topical preparations were made: The first preparation contained 5% (w/w) 2-di-isopropylaminoethanthiophosphate, the second preparation contained 5% (w/w) 2-diphenylaminoethanthiophosphate, the third preparation contained 5% (w/w) para-phenol-thiophosphate, the fourth preparation contained 5% (w/w) 2-di-isopropylaminoethanthiol, the fifth preparation contained 5% (w/w) 2-diphenylaminoethanthiol and the sixth preparation contained 5% (w/w) para-thiophenol, in a hydrophil cream vehicle. These six topical preparations were each applied to three separate areas, each with a surface area of 9 cm$^2$, on the upper back of six healthy volunteers with phototype IV. The hydrophil cream alone was applied on a separate area of the back of the same subjects and served as negative control. Applications were performed daily for six consecutive weeks. The skin lightening effect of the products was evaluated at the end of the study by a clinician blinded to the treatment identifications and through using a chromameter.

The first, second and third preparations were each respectively more effective than the fourth, fifth and sixth preparations regarding the skin depigmenting effect. The first second and third formulations induced no skin irritation during the study, while the fourth, fifth and sixth preparations each induced skin redness, dryness and sometimes itchiness on the test areas.

The first, second and third preparations were odorless, while the fourth, fifth and sixth preparations had an unpleasant skunky odor. Thus the thiophosphate depigmenting molecules were more effective and less irritant to the skin and were odorless compared to their non-phosphated thiol counterparts.

Example 2

Two female volunteers diagnosed with melasma and resistant to different topical depigmenting formulations containing hydroquinone or cysteamine were treated once daily for six weeks by the topical application of a preparation containing 5% (w/w) 2-isopropylaminoethanthiophosphate in a hydrophil cream base. Significant improvement of melasma lesions was observed in both patients at the end of the study. The improvement was confirmed by the patients and was also quantitatively confirmed by a chromametric examination before and after the treatment. No side effects were observed in the patients.

Example 3

Higher Depigmenting Efficacy in Comparison with Cysteamine-Phosphate

Cultured B16 melancytes were treated with 10 micromolar of cysteamine-phosphate or 2-di-isopropylaminoethanethiophosphate and the effect of each molecule on the inhibition of melanin synthesis was determined in comparison to the non-treated cells after 5 consecutives days of treatment.

It was shown that 2-di-isopropylaminoethanethiophosphate reduced the melanin content of viable B16 melanocytes to 85.5 microgram/ml compare to control which contained 105.7 microgram/ml of melanin ($p<0.001$, significant). While cysteamine phosphate at 10 micromolar concentration had no effect on the melanin content of viable B16 melanocytes.

Higher Efficacy in Comparison with Cysteamine and Cysteamine-Phosphate in vivo 2-di-isopropylaminoethanethiophosphate as well as cysteamine and cysteamine-phosphate were made into 5% (w/w) creams and were applied once daily to the skin of six human volunteers with phototypes III during six weeks. The vehicle alone was applied as the control. Skin colour was measured in each area before and after the treatment period using Dermacatch as the skin colorimeter. Melanin values were significantly reduced in all three cases (but not in the area treated with the vehicle alone). The order of depigmenting efficacy was: 2-di-isopropylaminoethanethiophosphate>>Cysteamine-phosphate>>Cysteamine Dermacatch Values for Vehicle Treated Skin
    Before treatment: 625+/±12
    After treatment: 634+/±6
Dermacatch Values for Cysteamine Treated Skin
    Before treatment: 623+/±14
    After treatment: 546+/±8
Dermacatch Values for Cysteamine Phosphate Treated Skin
    Before treatment: 626+/±10
    After treatment: 525+/±5
Dermacatch Values of 2-di-isopropylaminoethanethiophosphate Treated Skin
    Before treatment: 625+/±8

After treatment: 478+/±14

No Odor in Comparison to Cysteamine and Cysteamine-Phosphate

Cysteamine is a very mal-odorous molecule and gives a skunky odor to creams containing it. Cysteamine-phosphate is odorless in its dry powder form, but produces a bad odor in cream conditions. Although formulations, containing cysteamine, with reduced odor exist, however the odor is still present and bothersome to users. In contrast to cysteamine and cysteamine-phosphate, 2-di-isopropylaminoethanethiophosphate is odorless and does not produce any odor in cream formulations, which is a significant advantage over the other two molecules for use in topical products.

Higher Stability, No Colour Change of the Product

Both cysteamine and cysteamine-phosphate are unstable in cream conditions and are oxidized in a few hours to form an orange-red by-product that changes the colour of the creams. This colour change happens more rapidly (less than 10 minutes) in the case of exposure to temperatures higher than 30 degrees C. This undesirable colour change does not occur with 2-di-isopropylaminoethanethiophosphate even in the case of exposure to high temperatures (45 degrees C. for 7 days) and the cream containing this molecule remains intact regarding its colour.

The invention claimed is:

1. A skin and/or hair depigmentation composition comprising:
   a depigmentation effective amount of a thiophosphate derivative selected from the group consisting of 2-di-isopropylaminoethanethiophosphate, 2-diphenylaminoethanethiophosphate and para-phenol-thiophosphate or pharmaceutically acceptable salts thereof; and
   an acceptable carrier for topical, oral and/or parenteral administration.

2. The skin and/or hair depigmentation composition of claim 1, wherein said thiophosphate derivative is selected from the group consisting of 2-di-isopropylaminoethanethiophosphate, and 2-diphenylaminoethanethiophosphate.

3. The skin and/or hair depigmentation composition of claim 1, wherein said skin and hair are a mammal skin and hair.

4. The skin and/or hair depigmentation composition of claim 1, wherein said depigmentation composition is in a suitable form for topical application, selected from the group consisting of a lotion, a cream, a gel, a solution, a spray, a patch, a cleanser, a powder, an ointment, a wax, a lipstick, a soap, a shampoo, a bath gel, a bath oil, a bath bubble, a hydroalcoholic solution, a suspension, a scrub, a saturated pad, a skin or hair conditioning agent; or in a suitable form for oral administration to human comprising a tablet, a capsule, a powder, a syrup, a gel, a suspension, an aqueous or non-aqueous solution; or in a suitable form for parenteral administration, an injectable solution, inhalation spray, suppository or transdermal patch.

5. The skin and/or hair depigmentation composition of claim 1, wherein said composition further comprises a skin and/or hair benefit agent selected from the group consisting of alpha-hydroxy acids, beta-hydroxy acids, polyhydroxy acids, nicotinamide, kojic acid, arbutin, deoxyarbutin, depigmenting oligopeptides, soybean extract, licorice extract, phyllanthus emblica extract, Bellis perennis extract, glabridin, polyphenol antioxidants, thiolic antioxidants, cysteamine hydrochloride, hydroquinone, methimazole, pyridines, t-butyl hydroquinone, Vitamin C derivatives, Vitamin E, Vitamin B, dioic acids, retinoids, 4-substituted resorcinol, tranexamic acid, corticosteroids and mixtures thereof.

6. A method for reducing pigmentation of normal skin and/or hair, comprising topically applying the skin and/or hair depigmentation composition of claim 1 to the skin and/or hair of a subject in need thereof.

7. A method for reducing skin pigmentation disorders, comprising topically, orally or parenterally applying the skin depigmentation composition of claim 1 to the skin of a subject in need thereof.

8. The method of claim 7, wherein said pigmentation disorders are selected from the group consisting of hyperpigmentation, melasma, postinflammatory hyperpigmentation, solar or senile lentigo, freckles, drug induced hyperpigmentation, light induced hyperpigmentation and chemical induced hyperpigmentation.

* * * * *